United States Patent
Lentz et al.

[11] Patent Number: 6,036,724
[45] Date of Patent: Mar. 14, 2000

[54] PTFE VASCULAR GRAFT AND METHOD OF MANUFACTURE

[75] Inventors: David J. Lentz, Randolph; Jamie Henderson, Oakland; Edward J. Dormier, Rockaway; Richard J. Zdrahala, Montville, all of N.J.

[73] Assignee: Meadox Medicals, Inc., Natick, Mass.

[21] Appl. No.: 09/008,265

[22] Filed: Jan. 16, 1998

Related U.S. Application Data

[62] Division of application No. 08/588,052, Jan. 22, 1996, Pat. No. 5,800,512.

[51] Int. Cl.⁷ .................................................... A61F 2/06
[52] U.S. Cl. .................................................. 623/1; 623/901
[58] Field of Search .................................. 623/1, 12, 901; 600/36

[56] References Cited

U.S. PATENT DOCUMENTS

| | | |
|---|---|---|
| Re. 31,618 | 7/1984 | Mano et al. . |
| 4,082,893 | 4/1978 | Okita . |
| 4,177,334 | 12/1979 | Okita . |
| 4,250,138 | 2/1981 | Okita . |
| 4,385,093 | 5/1983 | Hubis . |
| 4,478,665 | 10/1984 | Hubis . |
| 4,478,898 | 10/1984 | Kato . |
| 4,482,516 | 11/1984 | Bowman et al. . |
| 4,576,608 | 3/1986 | Homsy . |
| 4,598,011 | 7/1986 | Bowman . |
| 4,743,480 | 5/1988 | Campbell et al. . |
| 4,816,339 | 3/1989 | Tu et al. . |
| 4,857,069 | 8/1989 | Kira . |
| 4,877,661 | 10/1989 | House et al. . |
| 4,955,899 | 9/1990 | Della Corna et al. . |
| 4,973,609 | 11/1990 | Browne . |
| 5,024,671 | 6/1991 | Tu et al. . |
| 5,026,513 | 6/1991 | House et al. . |
| 5,061,276 | 10/1991 | Tu et al. . |
| 5,152,782 | 10/1992 | Kowligi et al. . |
| 5,154,866 | 10/1992 | Honda et al. . |
| 5,181,903 | 1/1993 | Vann et al. ................................ 600/36 |
| 5,308,664 | 5/1994 | House et al. . |
| 5,358,678 | 10/1994 | Nakamura et al. . |
| 5,374,473 | 12/1994 | Knox et al. . |
| 5,433,909 | 7/1995 | Martakos et al. . |
| 5,437,900 | 8/1995 | Kuzowski . |
| 5,453,235 | 9/1995 | Calcote et al. . |
| 5,462,781 | 10/1995 | Zukowski . |
| 5,716,394 | 2/1998 | Bruchmann et al. ...................... 623/1 |
| 5,749,880 | 5/1998 | Banas et al. ............................ 606/198 |
| 5,824,046 | 10/1998 | Smith et al. ................................ 623/1 |
| 5,824,049 | 10/1998 | Ragheb et al. ............................. 623/1 |
| 5,824,054 | 10/1998 | Khosravi et al. ........................... 623/1 |
| 5,858,556 | 1/1999 | Eckert et al. .............................. 623/1 |

FOREIGN PATENT DOCUMENTS

| | | |
|---|---|---|
| 3-349850 | 12/1991 | Japan . |
| 3-352338 | 12/1991 | Japan . |
| 3-359922 | 12/1991 | Japan . |
| 4-28337 | 2/1992 | Japan . |
| 4-73847 | 3/1992 | Japan . |
| 4-280512 | 9/1992 | Japan . |
| 4-303034 | 12/1992 | Japan . |
| 6-343688 | 12/1994 | Japan . |
| 5-321443 | 1/1995 | Japan . |
| 5-243819 | 3/1995 | Japan . |
| WO 95/05277 | 2/1995 | WIPO . |
| WO 95/24304 | 9/1995 | WIPO . |

*Primary Examiner*—David H. Willse
*Assistant Examiner*—Suzette J. Jackson
*Attorney, Agent, or Firm*—Hoffmann & Baron, LLP

[57] ABSTRACT

An implantable microporous ePTFE tubular vascular graft exhibits long term patency, superior radial tensile strength and suture hole elongation resistance. The graft includes a first ePTFE tube and a second ePTFE tube circumferentially disposed over the first tube. The first ePTFE tube exhibits a porosity sufficient to promote cell endothelization tissue ingrowth and healing. The second ePTFE tube exhibits enhanced radial strength in excess of the radial tensile strength of the first tube.

10 Claims, 3 Drawing Sheets

PTFE VASCULAR GRAFT AND METHOD OF MANUFACTURE

This is a divisional of application Ser. No. 08/588,052, filed Jan. 22, 1996, now U.S. Pat. No. 5,800,512.

FIELD OF INVENTION

The present invention relates generally to a tubular implantable prosthesis such as vascular grafts and endoprostheses formed of porous polytetrafluorethylene. More particularly, the present invention relates to a multi-layered tubular vascular graft or endoprosthesis formed from expanded polytetrafluorethylene.

BACKGROUND OF THE INVENTION

It is well known to use extruded tubes of polytetrafluorethylene (PTFE) as implantable intraluminal prostheses, particularly vascular grafts. PTFE is particularly suitable as an implantable prosthesis as it exhibits superior biocompatibility. PTFE tubes may be used as vascular grafts in the replacement or repair of a blood vessel as PTFE exhibits low thrombogenicity. In vascular applications, the grafts are manufactured from expanded polytetrafluorethylene (ePTFE) tubes. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). A graft having a large IND enhances tissue ingrowth and cell endothelization as the graft is inherently more porous.

The art is replete with examples of microporous ePTFE tubes useful as vascular grafts. The porosity of an ePTFE vascular graft can be controlled by controlling the IND of the microporous structure of the tube. An increase in the IND within a given structure results in enhanced tissue ingrowth as well as cell endothelization along the inner surface thereof. However, such increase in the porosity of the tubular structure also results in reducing the overall radial tensile strength of the tube as well as reducing the ability for the graft to retain a suture placed therein during implantation. Also, such microporous tubular structures tend to exhibit low axial tear strength, so that a small tear or nick will tend to propagate along the length of the tube.

The art has seen attempts to increase the radial tensile and axial tear strength of microporous ePTFE tubes. These attempts seek to modify the structure of the extruded PTFE tubing during formation so that the resulting expanded tube has non-longitudinally aligned fibrils, thereby increasing both radial tensile strength as well as axial tear strength. U.S. Pat. No. 4,743,480 shows one attempt to reorient the fibrils of a resultant PTFE tube by modifying the extrusion process of the PTFE tube.

Other attempts to increase the radial tensile, as well as axial tear strength of a microporous ePTFE tube include forming the tubular graft of multiple layers placed over one another. Examples of multi-layered ePTFE tubular structures useful as implantable prostheses are shown in U.S. Pat. Nos. 4,816,338; 4,478,898 and 5,001,276. Other examples of multi-layered structures are shown in Japanese Patent Publication nos. 6-343,688 and 0-022,792.

While each of the above enumerated patents provides tubular graft structures exhibiting enhanced radial tensile strength, as well as enhanced axial tear strength, these structures all result in tubes exhibiting lower porosity. More specifically, the multi-layered ePTFE tubular structures of the prior art exhibit a smaller microporous structure overall, especially at the inner surface, and accordingly, a reduction in the ability of the graft to promote endothelization along the inner surface.

It is therefore desirable to provide a ePTFE vascular graft which exhibits increased porosity especially at the inner surface thereof while retaining a high degree of radial strength especially at the external surface thereof It is further desirable to produce an ePTFE vascular graft which exhibits increased porosity at the outer surface thereof while retaining a high degree of radial tensile and suture retention strengths.

SUMMARY OF THE INVENTION

It is an object of the present invention to provide an improved ePTFE vascular graft.

It is a further object of the present invention to provide a ePTFE vascular graft exhibiting an enhanced microporous structure while retaining superior strength.

It is a still further object of the present invention to provide an ePTFE tubular structure having an inner portion exhibiting enhanced porosity and an outer portion exhibiting enhanced radial tensile strength and suture elongation characteristics.

It is yet another object of the present invention to provide a multi-layered ePTFE tubular vascular graft having an inner layer which has a porosity sufficient to promote cell endothelization and an outer layer having a high degree of radial tensile strength.

It is an additional object of the present invention to provide a multi-layered ePTFE tubular vascular graft having an outer layer whose porosity is sufficient to promote enhanced cell growth and tissue incorporation, hence more rapid healing, and an inner layer having a high degree of strength.

In the efficient attainment of these and other objects, the present invention provides an implantable polytetrafluorethylene (PTFE) vascular graft. The graft includes a first ePTFE tubular structure, and a second ePTFE tubular structure circumferentially disposed exteriorly about the first tubular structure. The porosity and physical strength characteristics of each of the aforementioned tubular structures can be varied independently of each other. This results in a structure whose first ePTFE tubular structure exhibits a porosity sufficient to promote cell endothelization there along, while the second structure exhibits strength in excess of the strength of the first tubular structure. Alternatively the first ePTFE tubular structure exhibits strength in excess of the strength of the second tubular structure, while the second tubular structure exhibits a porosity sufficient to promote more rapid tissue incorporation.

As more particularly described by way of the preferred embodiment herein, the first and second PTFE tubular structures are formed of expanded polytetrafluoroethylene (ePTFE). Further, the second ePTFE tubular structure is adheringly supported over the first ePTFE tubular structure to form a composite tubular graft. The strength of this adhesion can be varied as desired to control the characteristics exhibited by the resultant composite structure.

In its method aspect, the present invention provides a method of forming a vascular graft. The method includes the steps of providing a first ePTFE tubular structure having a desired porosity and strength combination. A second ePTFE tubular structure is provided, also having the desired porosity and strength combination. The second ePTFE structure is disposed over the first ePTFE so as to define a composite vascular graft.

The method of the present invention also provides for the positioning of an intermediate structure between the first and second ePTFE tubular structures. Examples of such structures include an additional ePTFE layer and fibers or thin films of PTFE or other suitable polymers. This intermediate structure also contributes to the resultant porosity and strength of the vascular graft.

DETAILED DESCRIPTION OF THE PREFERRED EMBODIMENTS

The prosthesis of the preferred embodiments of the present invention is a multi-layered tubular structure which is particularly suited for use as an endoprosthesis or vascular graft. The prosthesis is formed of extruded polytetrafluoroethylene (PTFE) as PTFE exhibits superior biocompatability. Further, PTFE is particularly suitable for vascular applications as it exhibits low thrombogenicity. Tubes formed of extruded PTFE may be expanded to form ePTFE tubes where the ePTFE tubes have a fibrous state which is defined by elongated fibrils interconnected by spaced apart nodes. Such tubes are said to have a microporous structure, the porosity of which is determined by the distance between the surfaces of the nodes, referred to as the internodal distance (IND). Tubes having a large IND (greater than 40 microns) generally exhibit long term patency as the larger pores promote cell endothelization along the inner blood contacting surface. Tubes having lower IND (less than 40 microns) exhibit inferior healing characteristics, however they offer superior radial tensile and suture retention strengths desirable in a vascular graft. The present invention provides a composite tubular structure which promotes long term patency of the graft by providing for enhanced cell endothelization along the inner surface while exhibiting enhanced strength due to the presence of the outer layer.

Figure 1:
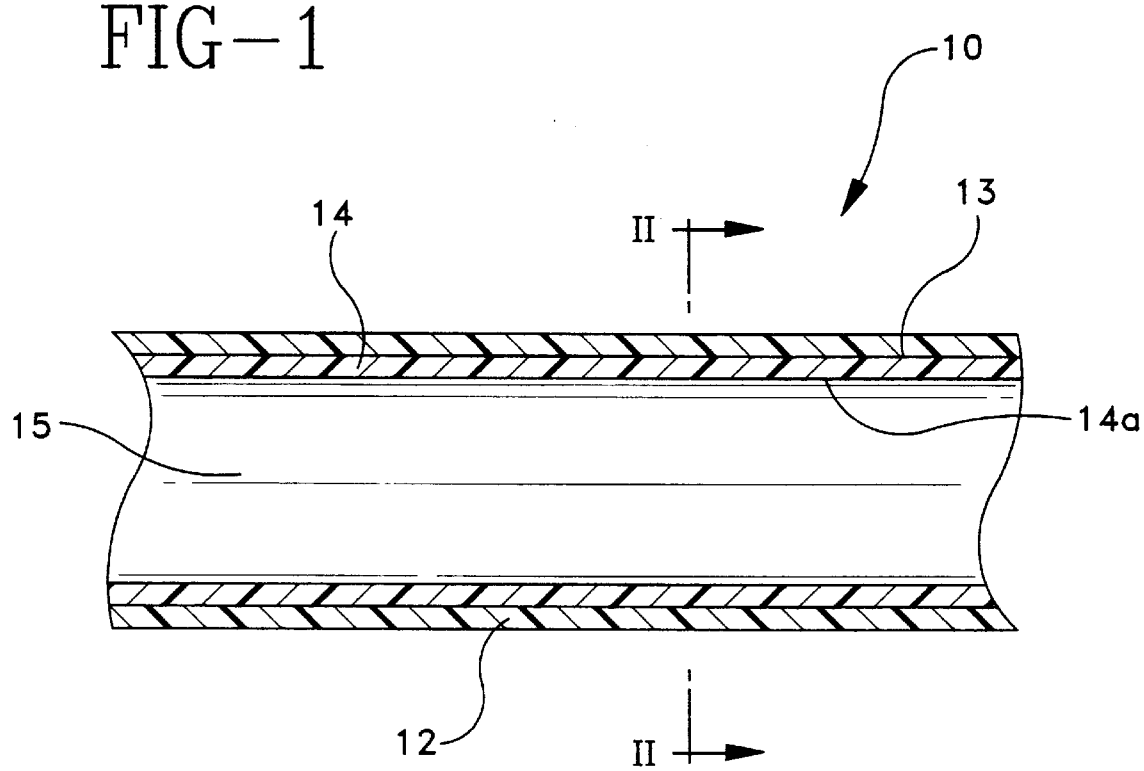
FIG. 1 is a schematic longitudinal cross-section of a multi-layer ePTFE vascular graft of the present invention.
Figure 2:
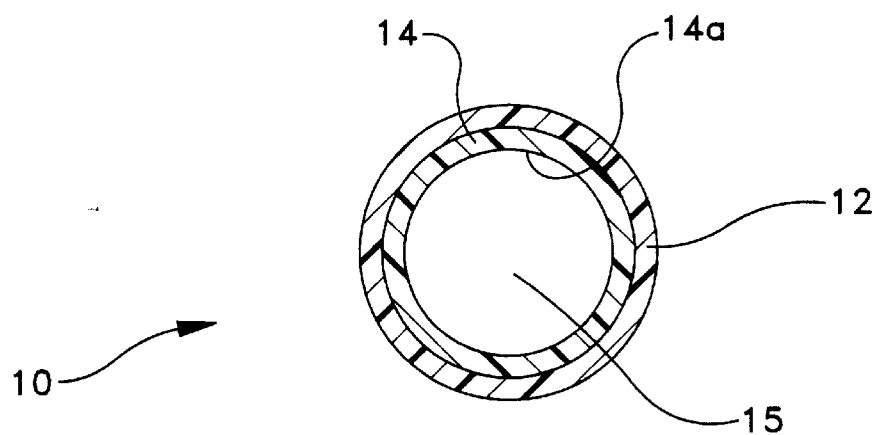
FIG. 2 is a longitudinal cross-section of an alternate embodiment of the present invention producing a multi-layer ePTFE vascular graft.

Referring to FIGS. 1 and 2 of the drawings, composite graft 10 of the present invention is shown. Graft 10 is a elongate tubular structure formed of PTFE. Graft 10 includes a pair of coaxially disposed ePTFE tubes 12 and 14, tube 12 being the outer tube and tube 14 being the inner tube. A central lumen 15 extends through composite graft 10, defined further by the inner wall 14a of inner tube 14, which permits the passage of blood through graft 10 once the graft is properly implanted in the vascular system.

Each tube 12 and 14 may be formed in a separate extrusion process. The process for the paste extrusion of PTFE tubes is well known in the extrusion art. Once extruded, the tubes are expanded to form ePTFE tubes. As will be described hereinbelow, the tubes are expanded using differing process parameters (rates, deformation levels, temperatures, etc) to develop the desired microporous structures. The specifically designed structure of the resulting composite tube has defined properties of strength and porosity which yield a graft 10 having long term patency and good healing characteristics as well as superior strength characteristics.

The present invention is designed to produce grafts with substantially different node/fibril structures with respect to the internal and external portions of the graft which are adjacent to the internal and external graft surfaces. As an example, the inner tube 14 is designed to have relatively high IND while the outer tube 12 is designed to have a lower IND. Further, a distinct porosity change is clearly defined at the interface 13 between tubes 12 and 14. The inner tube 14 having a higher IND to allow enhanced cell endothelization, while the outer tube 12 having a lower IND provides superior strength to the overall composite.

Figure 3:
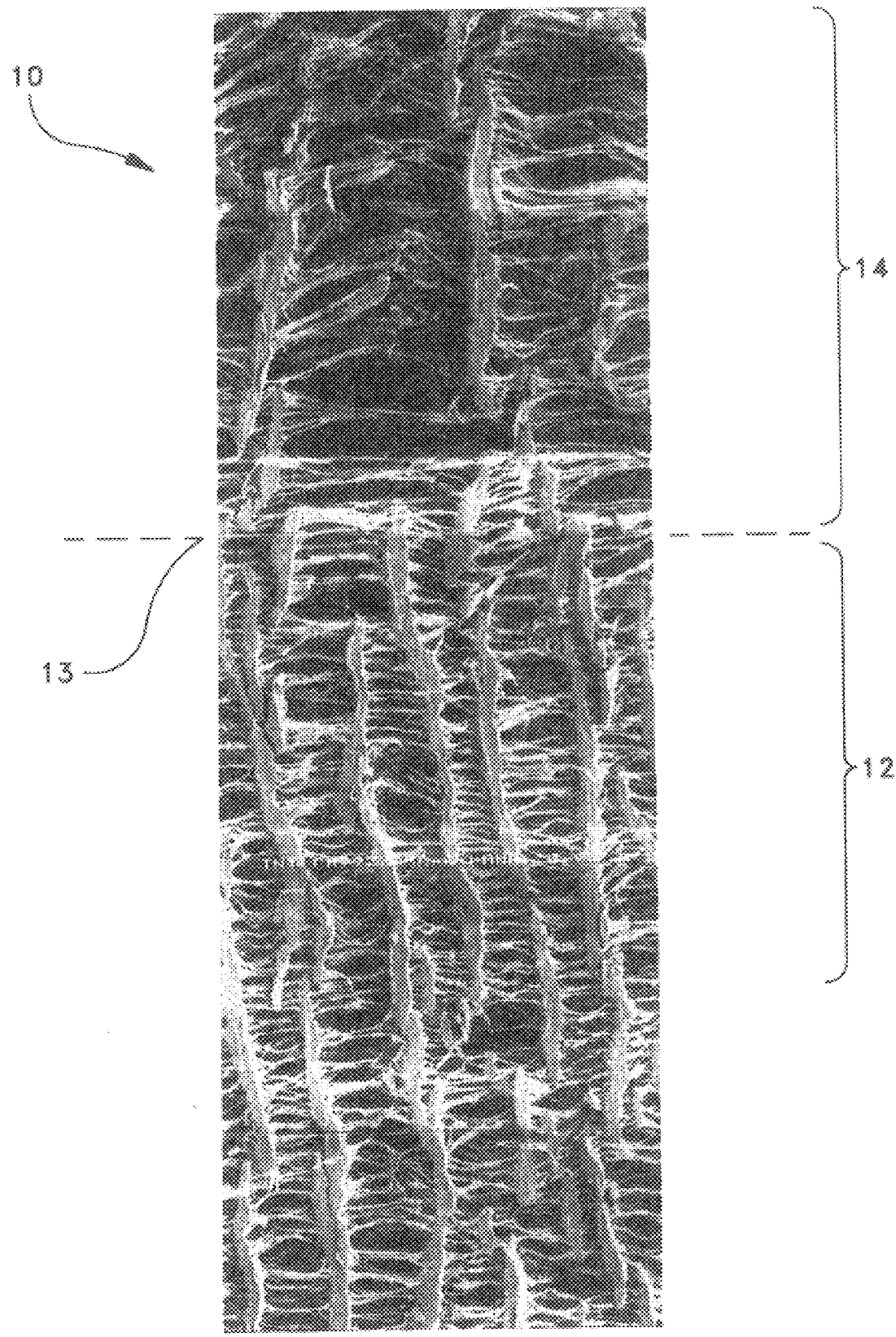
FIG. 3 is a scanning electron micrograph showing a cross-sectional view of a vascular graft produced using the present invention.

An electron micrograph of such a structure produced according to the present invention is shown in FIG. 3. The disparate IND's between the inner tube 14 and outer tube 12 are clearly evident, along with the step change in IND at the interface 13 between the inner tube 14 and outer tube 12. In this example, the strength of the interface 13 has been established by the processing conditions described below to fully adhere the inner tube 14 and outer tube together, hence preventing relative motion and providing enhanced strength.

Graft 10 of the present invention may be formed by expanding a thin wall inner tube 14 at a relatively high degree of elongation, on the order of approximately between 400 and 2000% elongation preferably from about between 700% and 900%. Tube 14 is expanded over a cylindrical mandrel (not shown), such as a stainless steel mandrel at a temperature of between room temperature and 645° F., preferably about 500° F. Tube 14 is preferably but not necessarily fully sintered after expansion. Sintering is typically accomplished at a temperature of between 645° F. and 800° F. preferably at about 660° F. and for a time of between about 5 minutes to 30 minutes, preferably about 15 minutes. The combination of the ePTFE tube 14 over the mandrel is then employed as a second mandrel, over which outer tube 12 is expanded. The ID of the outer tube 12 is selected so that it may be easily but tightly disposed over the OD of inner tube 14. The composite structure 10 is then sintered at preferably similar parameters. The level of elongation of outer tube 12 is lower than that of inner tube 14, approximately between 200% and 500% elongation preferably about 400%. The expansion and sintering of outer tube 12 over the inner tube 14 serves to adheringly bond the interface 13 between the two tubes, resulting in a single composite structure 10.

As shown in FIG. 3, the resulting composite structure has an inner surface defined by inner tube 14 which exhibits an IND of between 40 and 100 microns, spanned by moderate number of fibrils. Such microporous structure is sufficiently large so as to promote enhanced cell endothelization once blood flow is established through graft 10. Such cell endothelization enhances the long term patency of the graft.

The outer structure, defined by outer tube 12, has a smaller microporous structure, with IND of 15–35 microns and a substantial fibril density. Such outer structure results in an increase in the strength of the outer tube, and hence of the composite structure. Importantly, the outer surface defined by the outer tube 12 exhibits enhanced suture retention due to the smaller IND.

Furthermore, the resulting composite structure exhibits a sharp porosity change between the outer tube 12 and inner tube 14. This sharp porosity transition is achieved by providing an inner tube 14 having generally a given uniform porosity therealong and then providing a separate outer tube 14 having a resultant different porosity uniformly thereal-ong. Thus a distinct porosity change is exhibited on either side of the interface 13 defined between inner tube 14 and outer tube 12.

In addition, the forming process described above results in a bonded interface between inner tube 14 and outer tube 12. The interface exhibits sufficient interfacial strength resulting from the direct sintering of the outer tube 12 over the inner tube 14 so as to assure complete bonding of the two tubes. The strength of the interface between the two tubes may be independently varied through selection of processing conditions and relative dimensions of precursor extruded tubes 12 and 14 as desired to yield a range of performance.

The following examples serve to provide further appreciation of the invention but are not meant in any way to restrict the scope of the invention.

EXAMPLE I

A thin extruded tube having wall thickness of 0.41 mm and an inner diameter of 6.2 mm was expanded over a stainless steel mandrel at 500° F. to 900% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube/mandrel combination at 500° F. and 400% elongation. The composite was then sintered at 660° F. for 14 minutes, cooled and removed from the oven. The resultant composite tube had a wall thickness of 0.65 mm and ID of 5.8 mm.

EXAMPLE II

A thin extruded tube having wall thickness of 0.41 mm and an inner diameter of 6.2 mm was expanded over a stainless steel mandrel at 500° F. to 700% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube at 500° F. and 400% elongation. The composite was sintered at 660° F. for 14 minutes, cooled, and removed from the oven. The resultant composite tube had a wall thickness of 0.67 mm and an inner diameter of 5.8 mm.

Table I presents physical property data for a vascular graft of the type depicted in Example I described above. The composite graft was removed from the mandrel and subjected to standard testing of radial tensile strength and suture hole elongation. The radial strength of the 900%/400% composite graft is equivalent to a single layer 400% elongation graft and substantially stronger than a single layer 900% elongation graft, despite an overall thinner wall dimension. Additionally, the superior strength of the composite graft is demonstrated by the higher elongation capable of being borne by the graft prior to failure. The lower suture hole elongation, indicative of a smaller tear being caused by suturing and tensioning at a fixed value of 100 grams is clearly demonstrated for the graft prepared by the method of the current invention.

TABLE I

| Physical Property Measurement | 400% Elongation Single Layer Graft | 900%/400% Elongation Composite Graft | 900% Elongation Single Layer Graft |
| --- | --- | --- | --- |
| Radial Tensile Strength ($kg/mm^2$) | 0.48 | 0.48 | 0.2 |
| Radial Strain at Break (%) | 550 | 690 | 531 |
| Suture Hole Elongation (%) | 87 | 81 | 158 |
| Wall Thickness | 0.72 | 0.65 | 0.73 |

Figure 4:
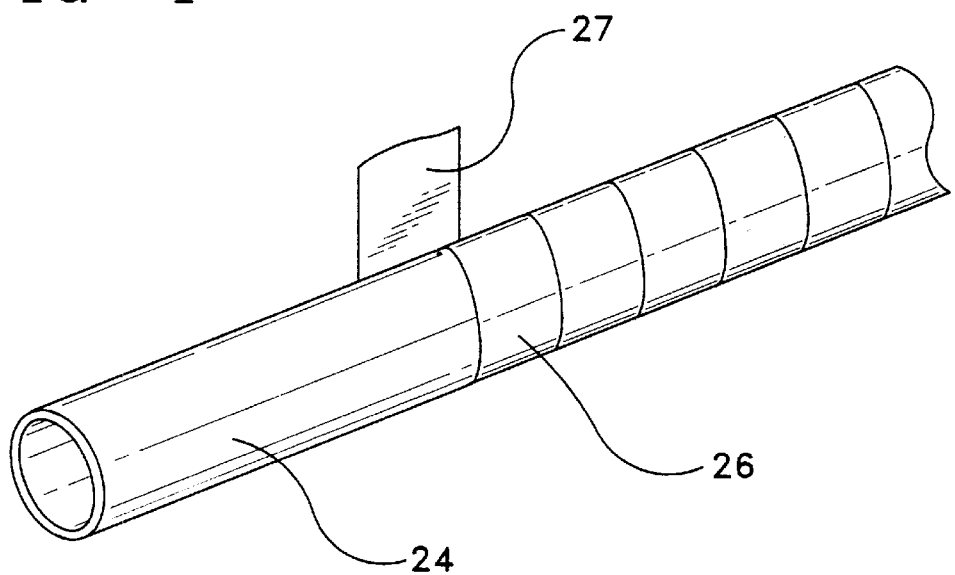
FIG. 4 is a perspective showing of one of the tubular structures of the graft of FIG. 1 over-wrapped with a layer of ePTFE tape.
Figure 5:
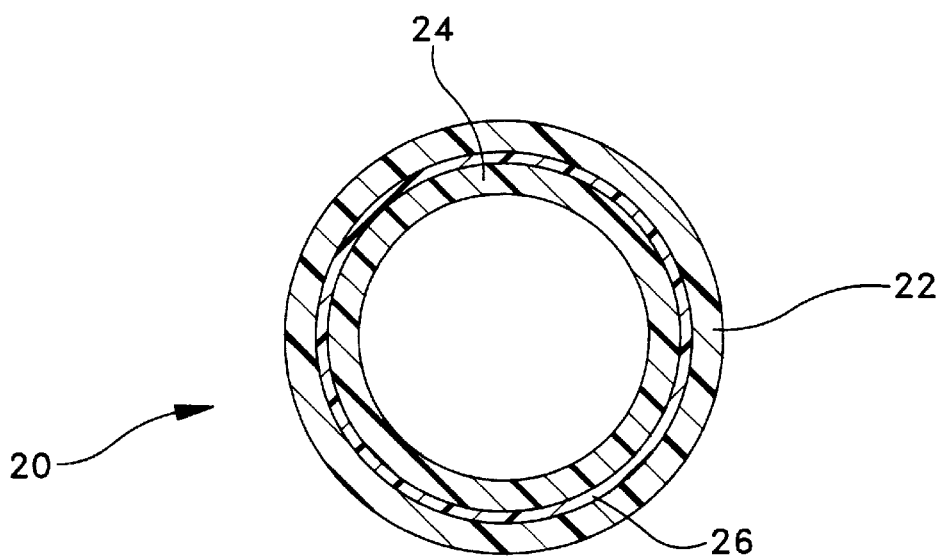
FIG. 5 is a cross-sectional showing of an alternate embodiment of the ePTFE vascular graft of the present invention. In this instance, the view is taken through the lines II—II of the view shown in FIG. 2.

Referring now to FIGS. 4 and 5, a further embodiment of the present invention is shown. Tubular graft 20 is a composite structure similar to graft 10 described above. Graft 20 includes an outer tube 22 and an inner tube 24 formed generally in the manner described above. In order to further control the porosity and strength of the graft 20, especially at the interface between outer tube 22 and inner tube 24, an additional layer may be employed in combination with outer tube 22 and inner tube 24.

As specifically shown in FIGS. 4 and 5, an additional layer 26 may be employed between inner tube 24 and outer tube 22. Layer 26 may include a helical wrap of ePTFE tape 27 placed over inner tube 24. The additional layer 26, however, may also exist as a sheet, film, yarn, monofilament or multi filament wrap, or additional tube. The additional layer 26 may consist of PTFE, FEP, or other suitable polymer composition to obtain the desired performance characteristics. Layer 26 may be used to impart enhanced properties of porosity and/or strength to the composite graft 20. For example, an additional layer 26 of ePTFE tape 27 having a low IND and wrapped orthogonally to the length direction of graft 20 would increase the radial strength of the resultant composite graft. Similarly, a layer of ePTFE having a high IND would increase the porosity of the composite structure thereby further promoting cell endothelization and/or tissue ingrowth.

As shown in FIG. 4, layer 26 is disposed between inner tube 24 and outer tube 22, and functions as an intermediate layer therein between. It is further contemplated that the additional layer may be employed over outer tube 22, or an additional layer may be used both over outer tube 22 and over inner tube 24.

Various changes to the foregoing described and shown structures would now be evident to those skilled in the art. Accordingly, the particularly disclosed scope of the invention is set forth in the following claims.

What is claimed is:

1. A method of forming a tubular vascular prosthesis comprising the steps of:
   (a) providing a first PTFE tubular structure having a given porosity sufficient to promote cell endothelization and a given strength;
   (b) providing a second PTFE tubular structure having a radial strength greater than the radial strength of said first PTFE tubular structure; and
   (c) disposing said second PTFE tubular structure over said first PTFE tubular structure to define a composite structure.

2. A method of claim 1 further including the step of:
   expanding said first PTFE tubular structure to form a first ePTFE structure.

3. A method of claim 2 further including the step of:

expanding said second PTFE tubular structure to form a second ePTFE structure.

4. A method of claim 3 wherein said steps of expanding said first PTFE tubular structure includes:

expanding said first PTFE tubular structure at an elongation of between about 400% and 2000%.

5. A method of claim 1 wherein said step of expanding said second PTFE tubular structure includes:

expanding said second PTFE tubular structure at an elongation of between 200% and 500%.

6. A method of claim 5 further including the steps of:

providing an additional structure; and positioning said additional structure over either said first PTFE tubular structure or said second PTFE tubular structure, or both said first and second tubular structures.

7. A method of claim 6 wherein said positioning step includes:

disposing said additional PTFE tubular structure over said first PTFE tubular structure.

8. A method of claim 7 wherein said additional structure is formed of PTFE.

9. A method of claim 1 wherein said providing step (a) further includes:

forming said first PTFE tubular structure over a mandrel.

10. A method of claim 9 wherein said disposing step (c) includes:

forming said second PTFE tubular structure over said first PTFE structure and said mandrel.

* * * * *